United States Patent [19]

Satterfield et al.

[11] Patent Number: 5,045,074
[45] Date of Patent: Sep. 3, 1991

[54] DIRECT DRIVE BLOOD DEFIBRINATION APPARATUS AND METHOD

[75] Inventors: William C. Satterfield, Elgin; Joan E. Foytik; Joe W. Bailey, both of Bastrop; William C. Schmidt, Fayetteville, all of Tex.

[73] Assignee: Board of Regents, The University of Texas System, Austin, Tex.

[21] Appl. No.: 353,125

[22] Filed: May 17, 1989

[51] Int. Cl.$^5$ ............................................. A61J 1/05
[52] U.S. Cl. ................................. 604/317; 604/903; 604/406; 604/320; 128/760; 128/765
[58] Field of Search ........................... 604/4–6, 604/19–21, 317–321, 403–406, 416, 903; 210/767, 780–784, 707; 128/760, 765

[56] References Cited

U.S. PATENT DOCUMENTS

| | | |
|---|---|---|
| 1,775,813 | 1/1929 | Cole . |
| 1,927,184 | 9/1933 | Poplawski . |
| 1,973,990 | 9/1934 | Marrinian ..................... 604/903 X |
| 2,020,252 | 11/1935 | Utterback et al. ................. 604/317 |
| 2,055,263 | 9/1936 | Robinson et al. . |
| 2,774,576 | 12/1956 | Frank . |
| 4,129,131 | 12/1978 | Naftulin ........................ 604/317 X |
| 4,437,472 | 3/1984 | Naftulin ........................ 604/320 X |
| 4,577,975 | 3/1986 | McCrory et al. . |
| 4,773,314 | 9/1988 | Fabbri . |

FOREIGN PATENT DOCUMENTS 202973 2/1939 Switzerland .

Primary Examiner—Robert A. Hafer
Assistant Examiner—Kerry Owens
Attorney, Agent, or Firm—Arnold, White & Durkee

[57] ABSTRACT

A direct drive blood defibrination unit and a method of using the unit are presented. The blood defibrination unit includes a vacuum bottle having input, vacuum, dispensing and drive ports therein. Contained within the bottle is a rotatable stir bar which is connected to a drive shaft which passes through the drive port of the vacuum bottle and is connected to a motor. A bacteria and vacuum seal surrounds the drive shaft adjacent the drive port in order to maintain the pressure differential between the inside and outside of the vacuum bottle without bacterial contamination. In operation, the input port of the vacuum bottle is connected to a source of blood to be defibrinated, and the vacuum port is connected to a source of vacuum. The stir bar is rotated during a blood collection time period, and is allowed to continue to rotate for a defibrination time period during which the input and vacuum ports are disconnected. After defibrination, the defibrinated blood is dispensed from the dispensing port. The present invention improves hematocrit of defibrinated blood without bacterial or fibrin contamination. In addition, the unit and method of the present invention decrease the time necessary to collect and defibrinate blood.

9 Claims, 2 Drawing Sheets

DIRECT DRIVE BLOOD DEFIBRINATION APPARATUS AND METHOD

The Government may own certain rights in the present invention pursuant to Grant CA-16672 from the National Cancer Institute.

BACKGROUND OF THE INVENTION

The present invention relates to direct drive blood defibrination apparatus and methods.

There are a wide range of medical research and clinical laboratory applications for defibrinated blood, including the production of blood agar plates, the isolation of human T lymphocytes using the Rosette assay, and minimum inhibitory concentration studies. Quality assurance standards of the ovine blood product require a relatively high hematocrit, on the order of at least 35%, and the complete absence of fibrin and bacteria. In a known ovine blood collection and defibrination technique, a magnetic stirrer used to indirectly drive a stir bar is used. Such indirectly driven stir bar defibrination units have proven unreliable since the stir bar can jump out of the magnetic field or even stop as a result of blood turbulence during collection, inconsistent vacuum within the collection chamber, or uneven fibrin clot formation around the stir bar. When the stir bar stops, a web of fiber immediately forms entrapping erythrocytes in the fibrin clot resulting in an undesirable increase in the size of the fibrin clot and a resultant reduction in the volume of defibrinated blood product. In addition, indirectly driven defibrination units tend to reduce blood hematocrit and often do not sufficiently remove blood fibrin.

Due to the unreliable and unpredictable nature of such indirectly driven defibrination units, excess blood must be drawn in order to insure production of a desired volume of acceptably defibrinated blood. Also, since hematocrit is adversely affected, more donor candidates must be screened. This results in an increased herd size, increased collection time and potential monetary loss from excess blood which cannot be used.

SUMMARY OF THE INVENTION

The present invention is direct drive defibrination unit and a method of using the direct drive defibrination unit, which result in reliable and predictable blood defibrination without bacterial contamination.

The invention includes a vacuum bottle which has input, vacuum, dispensing and drive ports therein. Within the vacuum bottle is a white high density polyethelyne plastic stir bar which is rotated by a drive shaft which extends through the drive port of the vacuum bottle. A bacteria and vacuum seal surrounds the drive shaft as it passes through the drive port and serves to keep bacteria from within the vacuum bottle, and to maintain a pressure differential between the inside and outside of the vacuum bottle. The input port of the vacuum bottle is connected to a source of blood to be defibrinated, for example a sheep. The vacuum port is connected to a source of vacuum, and the dispensing port, which remains closed during defibrination, is used to dispense defibrinated blood.

During operation, the input port is connected, through sterile tubing or the like and a hypodermic needle to the jugular vein of a sheep, and the vacuum input is connected to a source of vacuum. The stir bar is rotated while blood is being collected, and fibrin begins to collect on the stir bar. After blood collection is complete, the vacuum and input ports are disconnected, and the stir bar is allowed to continue to rotate for a defibrination period. After the defibrination period, the dispensing port is opened and the defibrinated blood is dispensed. An additional fibrin filter can be placed in the dispensing port, if desired.

Use of the present invention results in predictable and reliable defibrination of blood, without bacterial contamination, and with improved hematocrit. This allows use of sheep with lower initial hematocrit thereby improving herd utilization, greatly reduces the incidence of rejection of unacceptable defibrinated blood product, and reduces technician time necessary to collect and defibrinate blood, all of which result in a reduction in cost per unit of acceptable defibrinated blood.

DETAILED DESCRIPTION OF THE PREFERRED EMBODIMENTS

Figure 1:
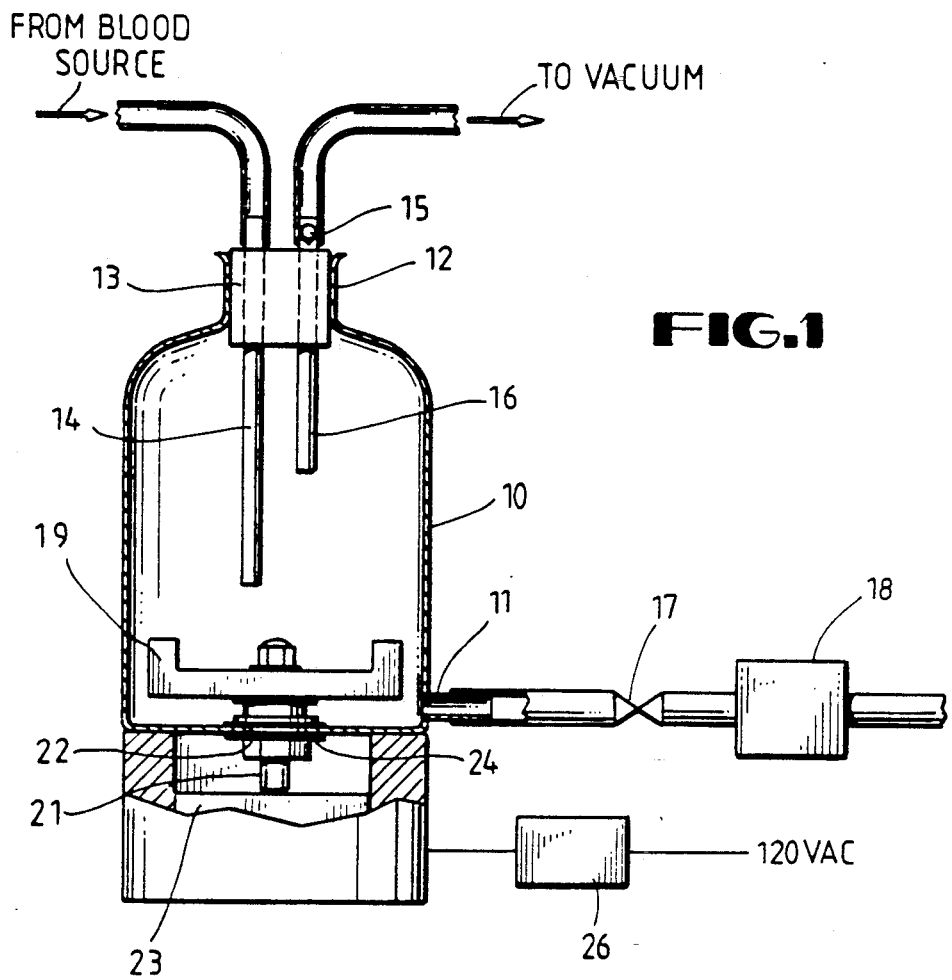
FIG. 1 is the direct drive defibrination unit according to the present invention.

Referring to FIG. 1, the direct defibrination unit of the present invention is shown. The invention includes heavy-walled glass aspirator bottle 10 including a tubing outlet used as dispensing output 11. In a neck 12 of bottle 10 is inserted two-hole stopper 13. Through one hole of stopper 13 passes input tube 14, and through the other hole of stopper 13 passes vacuum tube 16. Within vacuum tube 16, is cotton filter 15 which serves as a bacterial filter. Input tube 14 is connected to a source of blood (not shown) to be defibrinated. Vacuum tube 16 is connected to a source of negative pressure or vacuum (not shown).

Dispensing output 11 is connected through valve 17, which can be a clamp or other functionally equivalent valve structure, to in-line filter 18. Filter 18 is preferably a polypropylene mesh filter having a mesh size of 210 microns.

Located in the bottom of aspirator bottle 10 is stir bar 19 which is fixed to drive shaft 21. Drive shaft 21 passes through hole 22 formed in the bottom of aspirator bottle 10, and is connected to be rotated by motor 23. Surrounding shaft 21 as it passes through hole 22 of bottle 10 is bacteria and vacuum seal 24, the details of which will be described in more detail below with reference to FIG. 2. Motor 23 is preferably an electric motor, and can be a Waring commercial blender base type 7011, model 31BL92. Motor 23 is connected to a source of electrical power through rheostat 26 which is used to control the speed of motor 23, and in turn, the speed of drive shaft 21 and stir bar 19.

Figure 2:
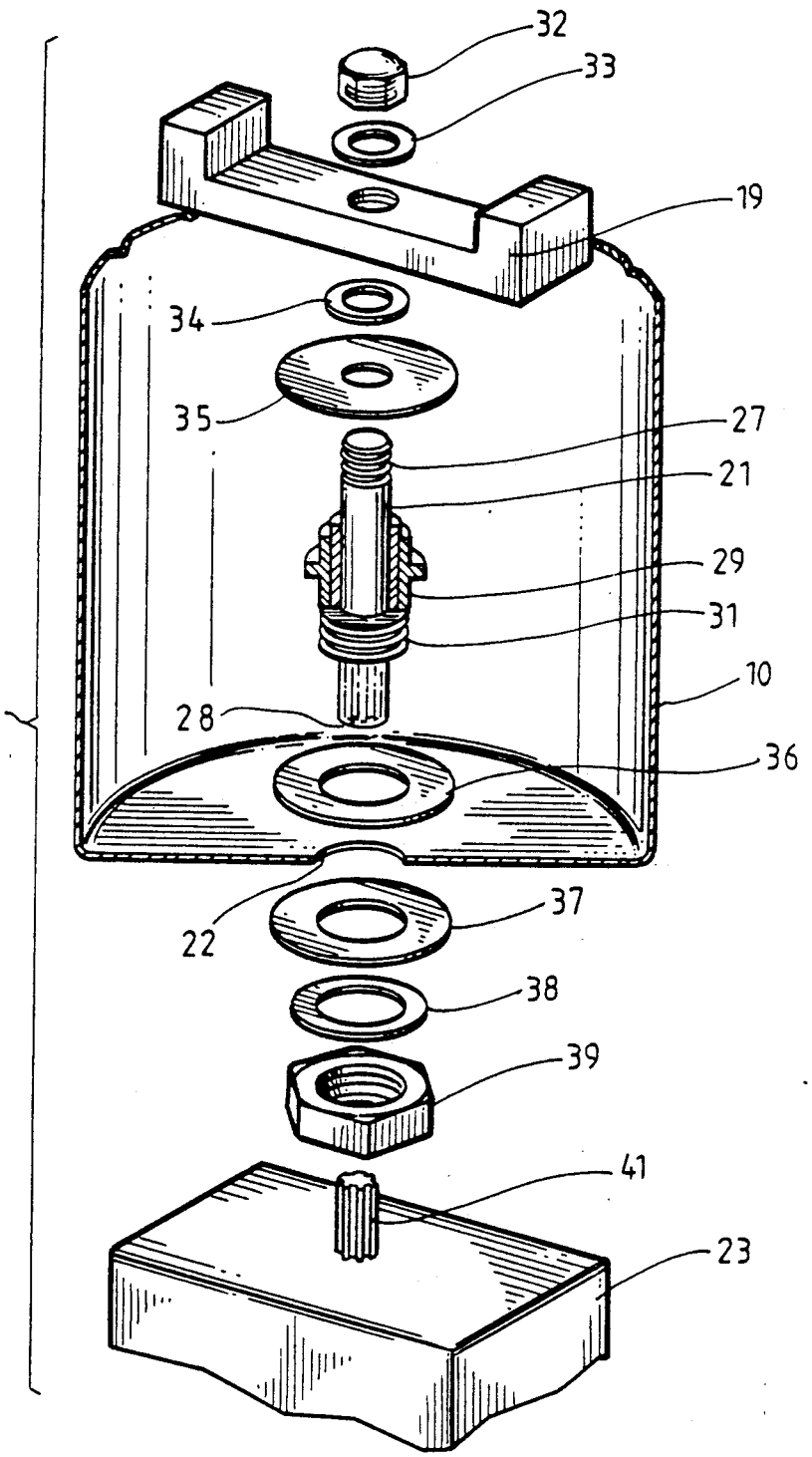
FIG. 2 is an exploded view of the configuration of the stir bar, drive shaft and vacuum seal of the unit of FIG. 1.

Referring now to FIG. 2, the details of the configuration of stir bar 19, drive shaft 21 and bacteria and vacuum seal 24 will be explained. Drive shaft 21 includes threaded end 27 and internally splined end 28. Drive shaft 21 is contained and rotates within drive shaft housing 29. Drive shaft housing 29 includes threaded bottom portion 31. Stir bar 19 is fixed to threaded end 27 of drive shaft 21 by use of drive shaft nut 32 and rubber gasket spacers 33-35. Rubber gasket 36 is placed around drive shaft housing 29, and threaded end 31 of drive shaft housing 29 is passed through hole 22 of aspirator bottle 10. Rubber gasket 37 and stainless steel washer 38 are then placed over threaded end 31 of drive shaft housing 29 and housing nut 39 is then threaded and tightened onto threaded end 31 of drive shaft housing 29. The internally splined end 28 of drive shaft 21 is then placed on splined shaft 41 of motor 23. Thus, as splined shaft 41 of motor 23 rotates, stir bar 19 also rotates. Rubber gaskets 36 and 37 together provide a bacteria and vacuum-tight seal between the interior and exterior of aspirator bottle 10 while stir bar 19 is rotatably driven by motor 23.

Figure 3:
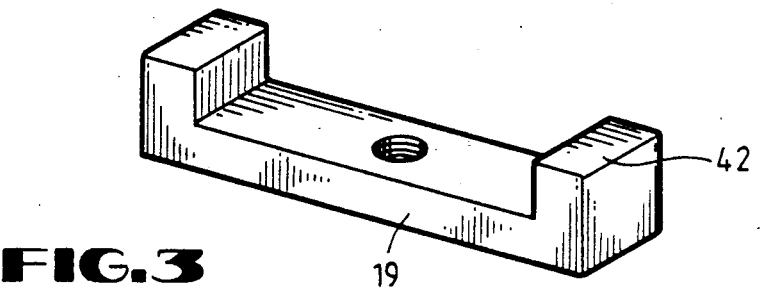
FIG. 3 is the stir bar of FIGS. 1 and 2.

Referring now to FIG. 3, stir bar 19 is explained in more detail. Stir bar 19 is preferably approximately 80 mm long and approximately 13 mm wide. Fingers 42 of stir bar 19 extend upwardly approximately 16 mm and are approximately 19 mm long. It should be understood that other dimensions will work without departing from the spirit and scope and the present invention. The preferred material for stir bar 19 is white high density polyethelyne plastic, however, other materials, such as stainless steel, can also be used.

Referring again to FIG. 1, in operation, input tube 14 is connected, through a hypodermic needle, or similar device (not shown) to the jugular vein of an appropriately prepared sheep. Vacuum tube 16 is connected to a source of vacuum (not shown) which is preferably approximately 10 inches of mercury. The amount of vacuum applied to vacuum tube 16 is chosen to draw blood in a reasonable amount of time without collapsing the vein from which the blood is being collected.

While blood is being collected, rheostat 26 is adjusted so that motor 23 spins stir bar 19 at a speed sufficient to defibrinate blood contained within aspirator bottle 10, without hemolyzing the blood. Acceptable rotational speed for stir bar 19 has been determined to be between 500 and 750 revolutions per minute. Other rotational speeds may also be acceptable.

The volume of aspirator bottle 10 is typically one liter, and blood collection is stopped after approximately 800 ml of blood have been collected, although it is understood that a greater or lesser volume could be collected without departing from the scope of the invention. The collection time period lasts for approximately five minutes. After the collection time period, input tube 14 and vacuum tube 16 are closed, and stir bar 19 is allowed to rotate for a defibrination time period of approximately 25 minutes. After the defibrination time period, valve 17 is opened and defibrinated blood is dispensed through dispensing port 11 and filter 18. It should be emphasized that other collection and defibrination time periods can be used without departing from the scope of the invention.

Comparing the present invention with indirectly (magnetically) driven defibrination units, the present invention exhibits marked improvements. Over a one year time period, during which an initial volume of approximately 182,500 ml of ovine blood was defibrinated to produce approximately 98,350 ml of defibrinated blood using an indirectly driven defibrination unit comprising a Lab-line Instruments, Inc., No. 1262 Multi-Magnistir type magnetic stirrer, for a defibrination efficiency (ratio of defibrinated volume to initial volume) of 54%. In addition, approximately 16% of the defibrinated blood was rejected due to inadequate hematocrit or excess fibrin content. In contrast, during a three month trial period, using the presently claimed invention, an initial volume of approximately 8,050 ml of ovine blood was defibrinated to produce approximately 5,800 ml of defibrinated blood for a defibrination efficiency of 72%, without any rejected for inadequate hematocrit, excessive fibrin content or bacterial contamination.

Table I presents a normalized comparison between the indirect drive defibrination method of the prior art, and the direct drive defibrination method of the present invention.

TABLE I

| METHOD | Total Initial Volume (ml) | Average Initial Volume (ml) | Average Dispensed Volume (ml) | Efficiency | Average Initial Hct | Average Dispensed Hct | Percent Rejected |
|---|---|---|---|---|---|---|---|
| INDIRECT DRIVE | 182,500 | 846 | 456 | 54% | 36.3% | 34.5% | 16% |
| DIRECT DRIVE | 8,050 | 805 | 580 | 72% | 35.6% | 36.2% | 0% |

As can be seen from Table I, the present direct drive method results in an increase in hematocrit of approximately 2% whereas the indirect drive method results in a decrease in hematocrit of approximately 5%. Thus, use of the direct drive method of the present invention allows ovine blood with a lower initial hematocrit to be used, thereby improving herd use and reducing the time necessary to screen acceptable donor candidates. In addition, the defibrination efficiency of the presently claimed invention, which is the ratio of the dispensed volume to the initial volume, is 72% compared with 54% defibrination efficiency of the indirect drive method. Also, the indirect drive method resulted in approximately 16% rejection because of low hematocrit or excessive fibrin content, whereas the direct drive defibrination method of the present invention resulted in rejection of no defibrinated blood.

While the present invention has been described with reference to a single preferred embodiment, it will be understood by those of ordinary skill in the art that modifications, additions and deletions can be made to the disclosed apparatus and method without departing from the spirit and scope of the invention.

What is claimed is:

1. A direct drive blood defibrination unit comprising:
   a vacuum bottle having an input port connectable to a source of blood to be defibrinated, a vacuum port connectable to a source of vacuum, and a drive port;
   a stir bar located within said vacuum bottle;
   a rotatable drive shaft connected to said stir bar and passing through said drive port, said stir bar being rotated when said drive shaft rotates;
   a bacteria and vacuum seal surrounding said drive shaft adjacent to said drive port, for maintaining a pressure differential between an interior and an exterior of said vacuum bottle without bacterial contamination; and
   a motor for rotating said drive shaft.

2. A defibrination unit as recited in claim 1, wherein said vacuum bottle further includes a defibrinated blood dispensing port.

3. A defibrination unit as recited in claim 2, further comprising a fibrin filter connected to said dispensing port.

4. A defibrination unit as recited in claim 3, wherein said filter is polypropylene mesh filter.

5. A blood defibrination unit as recited in claim 1, wherein said stir bar is high density polyethelyne plastic.

6. A method of defibrinating blood, comprising the steps of:
 providing a vacuum bottle including an input port, a vacuum port, a dispensing port, and a drive port;
 providing a stir bar located within said vacuum bottle and connected to a drive shaft which passes through said drive port;
 providing a bacteria and vacuum seal surrounding said drive shaft adjacent said drive port;
 rotating said drive shaft and stir bar;
 connecting said input port to a source of blood to be defibrinated;
 connecting said vacuum port to a source of vacuum;
 collecting blood from said source of blood for a collection time period;
 disconnecting said input port from said source of blood, and disconnecting said vacuum port from said source of vacuum;
 maintaining rotation of said drive shaft and stir bar for a defibrination time period; and
 dispensing defibrinated blood from said dispensing port after said defibrination time period.

7. A method as recited in claim 4 wherein said rotating step comprises rotating said drive shaft at a rotational speed between 500 and 750 revolutions per minute.

8. A method as recited in claim 4 wherein said collection time period is shorter than said defibrination time period.

9. A method as recited in claim 6 wherein said source of vacuum is at a pressure of approximately ten inches of mercury.

* * * * *

UNITED STATES PATENT AND TRADEMARK OFFICE
CERTIFICATE OF CORRECTION

PATENT NO. : 5,045,074

DATED : September 3, 1991

INVENTOR(S) : Satterfield, et al

It is certified that error appears in the above-identified patent and that said Letters Patent is hereby corrected as shown below:

Column 5, line 11, change "polyethelyne" to --polyethylene--.

Column 3, line 30, change "polyethelyne" to --polyethylene--.

Signed and Sealed this

Second Day of March, 1993

*Attest:*

STEPHEN G. KUNIN

*Attesting Officer*  *Acting Commissioner of Patents and Trademarks*